United States Patent [19]

Birks et al.

[11] 3,963,439

[45] June 15, 1976

[54] MULTIELECTRODE APPARATUS AND TECHNIQUES TO PREPARE ALIGNED ASBESTOS FIBERS ON A THIN SUBSTRATE

[75] Inventors: Laverne S. Birks, Potomac, Md.; Mohammad Fatemi, McLean, Va.

[73] Assignee: The United States of America as represented by the Secretary of the Navy, Washington, D.C.

[22] Filed: Sept. 5, 1975

[21] Appl. No.: 610,728

[52] U.S. Cl.......................... 23/230 PC; 23/253 PC; 264/108

[51] Int. Cl.²..................... B29D 3/02; G01N 23/20; G01N 31/06; G01N 31/12

[58] Field of Search.................. 23/230 PC, 253 PC; 264/108

[56] References Cited

UNITED STATES PATENTS 3,497,419 2/1970 Winer et al. ........................ 162/192

OTHER PUBLICATIONS

A. L. Rickards, Anal. Chem. 45, 809 (1973).

A. L. Rickards, Anal. Chem. 44, 1872 (1972).

*Primary Examiner*—Robert M. Reese

*Attorney, Agent, or Firm*—R. S. Sciascia; Philip Schneider; Melvin L. Crane

[57] ABSTRACT

A method of forming parallel aligned chrysotile asbestos fibers on a thin substrate for use in a system for identifying the chrysotile asbestos in air pollution samples. The system comprises a collimated x-ray beam which is incident on the parallel aligned asbestos fibers. Diffracted x-rays are detected by an adjustable proportional counter set at the diffraction line position for the (002) plane. Background intensity may be detected by a second adjustable counter set above the axis at the same angle 2*θ*, or the sample may be rotated 90° and the one detector used to detect diffracted and background x-rays.

3 Claims, 5 Drawing Figures

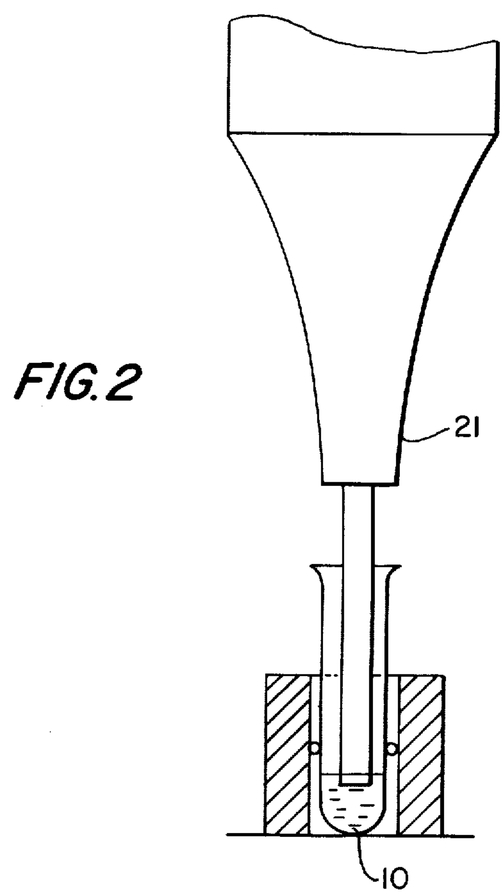
FIG. 2
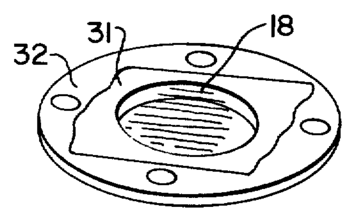
FIG. 4
FIG. 5
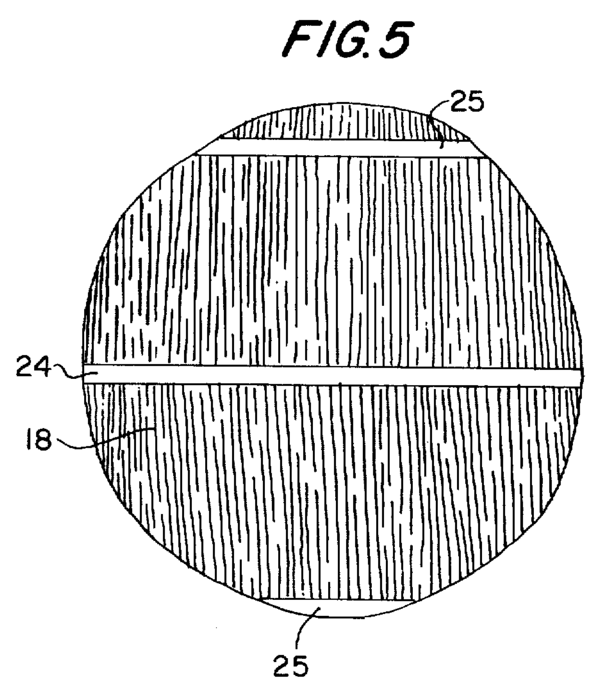

MULTIELECTRODE APPARATUS AND TECHNIQUES TO PREPARE ALIGNED ASBESTOS FIBERS ON A THIN SUBSTRATE

CROSS REFERENCE TO RELATED APPLICATION

This application is related to U.S. Application Ser. Nos. 610,730 and 610,729 filed on even date herewith.

BACKGROUND OF THE INVENTION

This invention relates to methods of detecting asbestos and more particularly to the preparation of asbestos samples for use in x-ray optics for measuring the asbestos within an air sample.

Heretofore analysis of elements, samples of materials, crystals, etc., have been carried out by x-ray optics since it is well known that they have a characteristic x-ray pattern. Most fibers other than asbestos are single crystals with a major axis along the fiber direction. Preferred orientation is observed for planes normal to the fiber axis but not for planes parallel to the axis. Thus the measurement of asbestos fibers are very difficult especially in a mixed sample.

One factor which makes measurement of asbestos difficult is the quantity which can be collected from a reasonable amount of air is far too small to measure with x-ray film cameras. Therefore diffractometers with electronic detectors are required, however other problems are introduced because of the peculiar morphology of crystalline matter. Chrysotile asbestos, like all crystals, has a characteristic x-ray diffraction pattern. However, platy serpentines has almost exactly the same x-ray pattern as chrysotile and many other clay minerals have very similar patterns. It has been determined that the morphology of chrysotile asbestos is like that of a "rolled up" sheet of crystalline matter with the *a*-axis parallel to the fiber axis, the *c*-axis is nearly perpendicular to the "tubular" wall, with the *b*-axis perpendicular to *a* and *c* axis. Thus, the axes (*b* and *c*) take different orientations depending on where on the fiber they are set up. Preferred orientation can be observed from the planes parallel to the fiber axis using the well known x-ray diffraction camera technique, however such methods cannot be adapted to airborn asbestos samples since it is not possible to form the fibers in the required small bundles. Further, it has been determined that even with an oriented sample the major crystal plane (002) diffracts equally well for either orientation. Therefore well known x-ray optics cannot be used for detecting asbestos in samples. A suitable system has been set forth in a publication NRL Report 7874, Quantitative Analysis of Airborn Asbestos by X-Ray Diffraction, by L.S. Birks and M. Fatemi, J.V. Gilfrich and E.T. Johnson, Naval Research Laboratory, Washington, D.C. 20375, which forms a part of this specification. U.S. Pat. No. 3,497,419 is directed to electrostatic alignment of asbestos fibers. This approach to alignment of asbestos fibers is not directly applicable to the present invention because the patent is concerned with long, silky industrial fibers and with large quantities of material. This invention is concerned with measurement of aerosol and other small samples to determine the presence and quantity of small asbestos elements in the sample.

SUMMARY OF THE INVENTION

This invention is directed to a method of aligning asbestos fibers for use in a special x-ray diffraction geometry for distinguishing chrysotile asbestos from serpentine and other clay minerals. The x-ray method requires alignment of the chrysotile fibers within a ring shaped holder and then aligning the holder for a special detection technique for identifying the presence of asbestos in a sample. The system is suitable for detecting 0.2$\mu$g asbestos in the absence of extraneous material for real air samples.

BRIEF DESCRIPTION OF THE DRAWING

FIG. 2 illustrates an ultrasonic "cell" disrupter with the probe inserted in a small sample of liquid containing dispersed asbestos.

FIG. 4 illustrates aligned fibers on a collodion film on a ring type sample holder.

FIG. 5 illustrates an optical macrograph illustrating the alignment of asbestos fibers within the electrode assembly.

DETAILED DESCRIPTION OF THE DRAWING

In carrying out the method of this invention it was first necessary to develop a new x-ray optics system for measuring the samples and to prepare a calibration standard from known amounts of asbestos samples. The x-ray optics system and method are contained in a copending application identified as Ser. No. 610,730 filed on even date herewith.

Figure 1:
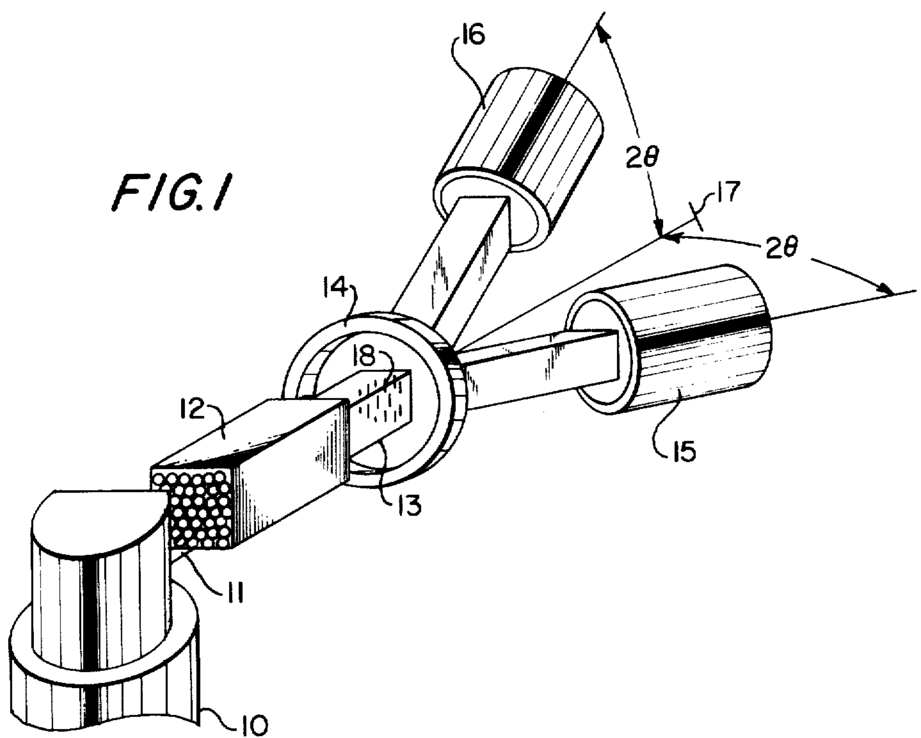
FIG. 1 illustrates an x-ray optic system in which the aligned fiber holder is placed for quantitative measurement of the aligned asbestos sample.

The x-ray optics system is shown in FIG. 1 and as shown the system includes a spectrograph type x-ray tube 10 which generates an x-ray beam 11 in the horizontal plane which has a large cross sectional beam area. The beam is directed into a tubular collimator 12 which collimates the x-ray beam into a broad beam of parallel rays 13. The collimated beam is directed onto an aligned asbestos sample 14 which is mounted with the fibers perpendicular to the x-ray beam and with the fibers aligned parallel to each other in the vertical plane. The x-ray beam is diffracted by the asbestos fibers into a normal mode detector 15 which measures the diffracted signal to the right of the normal beam path, plus any scattering due to the substrate. A second detector 16 is positioned above the main beam in the parallel mode and measures scattering alone. The detector 16 is positioned at the same angle $2\theta$ above the main beam path as the detector 15 is placed to the right of the main beam path. A beam stop 17 is provided to absorb the main beam path x-rays to avoid harmful injury to personnel who may otherwise be affected. The detectors 15 and 16 may be standard proportional counters set at the desired diffraction line and adjustable relative to the axis for detection of different diffraction angles $2\theta$.

In carrying out the method, the asbestos fibers 18 shown in FIGS. 4 and 5 are specifically orientated in substantially parallel alignment on a thin substrate with fibers spread over an area of about one centimeter. Therefore the x-ray beam should have a broad cross section.

U.S. Pat. No. 3,497,419 is directed to electrostatic alignment of asbestos fibers. This approach to alignment of asbestos fibers is not directly applicable to the present invention because the patent is concerned with long, silky industrial fibers and with large quantities of material. This invention is concerned with measurement of aerosol and other small samples to determine the presence and quantity of small asbestos elements in the sample.

In carrying out this invention to determine the unknown amount of asbestos in a sample, it was first necessary to prepare a sample with a known quantity of asbestos in order to provide a calibration standard. The following process was used to set up a pure asbestos calibration standard. Further, since the asbestos fibers are "silky" by nature, it has been determined that it is necessary to break the asbestos fibers down to fibril size to achieve best results.

The following method is carried out to break down the fibers to fibril size and to prepare a calibration sample.

Figure 3:
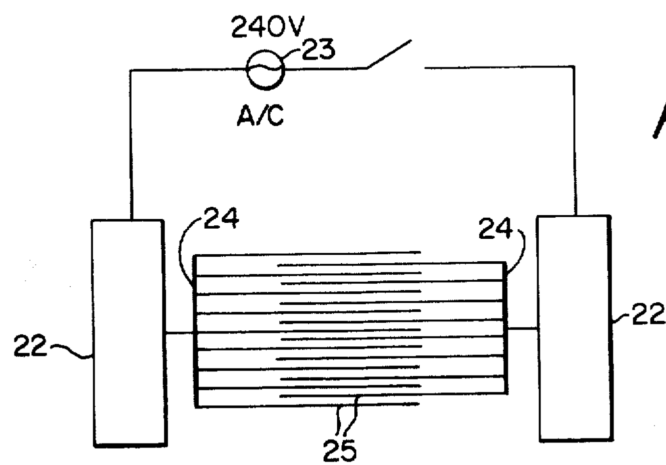
FIG. 3 illustrates a special multielectrode grid used in the alignment of asbestos fibers.

About 4 mg of UICC standard chrysotile asbestos fibers are placed in a wetting agent such as ½ ml of 1% Aerosol OT solution in water. Aerosol OT is a trade name of American Cynamid Co., which is dioctyl sodium sulfosuccinate. (The Aerosol OT is necessary as a dispersing agent). The suspension is sonicated for about 45 minutes at 100 watts power using a "cell disrupter" 21, as shown schematically in FIG. 2 for reducing the size of the fibers to 1–4$\mu$m long with a 0.1$\mu$m diameter. A suitable "cell disrupter" is a model No. 16–850 manufactured by the Virtiz Company. The sonicated suspension is diluted with water to 500 ml making the asbestos concentration 6$\mu$g/ml. A 25 ml aliquot of the diluted suspension (150$\mu$g of asbestos) is vacuum filtered onto a 25 mm diameter disk 0.45 – 0.50 mm pore size of millipore filter membrane. The disk of millipore is folded, placed into a test tube and ashed for about 2½ hours in a low-temperature radio-frequency asher such as a Perkin-Elmer No. Coleman 40. Subsequent to ashing 30 drops of 0.001% solution of parlodion (cellulose nitrate) in distilled amyl acetate is added to the ashed residue. The suspension is then sonicated for about 8 minutes to insure a homogeneous distribution of asbestos. One drop of the latter suspension containing about 5$\mu$g asbestos is placed onto a special grid, having parallel spaced electrodes with a spacing of about 0.8 mm. FIG. 3, which includes conductors 22 which are connected to a power source 23. The conductors are connected to feeder electrodes 24 to which one end of grid electrodes 25 are alternately connected. The power source may be 240 volts D.C. or A.C. The assembly is left undisturbed with the power applied until the droplet has completely dried. The power is then switched off and the electrodes are examined under an optical microscope for any unusual flaws in the sample. Electrodes are described in Ser. No. 610729.

Application of the power to the electrode of the grid causes the asbestos fibers to align themselves substantially parallel to each other and perpendicular to the grid wires. Therefore when the droplet has dried the asbestos fibers will remain aligned as set forth above.

A solution of 2.5% parlodion in amyl acetate is sprayed gently onto the dried sample to embed the fibers in a thin plastic film. The sprayed film is allowed to dry in a dust-free environment and subsequently stripped off the microelectrode assembly by dipping the grid into water in which the film with the aligned asbestos fibers attached floats to the surface of the water. The film 31 is picked up by a ring-shaped lucite holder 32 making sure that the film is wrinkle free and centrally aligned on the ring-shaped holder. The film is permitted to dry and is ready for measurement of the asbestos fibers. It has been determined that a thin film minimizes the background intensity contributed by x-ray scattering from the film during measurement.

The sample is then placed in the above described x-ray analyser and signal measurements are made which include signal and background as well as background. Samples containing different quantities of asbestos may be prepared and calibration curve for the different quantities may be made.

FIG. 5 illustrates a 50× micrograph of aligned fibers showing their uniform distribution between three electrode conductors 25.

Once the asbestos calibration standard has been made from known amounts of asbestos, analysis of actual particulate collections for asbestos content may be made. The unknown sample preparation is not completely the same as for the calibration samples because the unknown samples contain particulate matter other than asbestos. It has been determined that the sensitivity of the x-ray method is sufficient to give a limit of detection of 0.4$\mu$g for a 500 second counting time for samples containing extraneous matter.

In preparing samples containing pollutant asbestos, the pollutant sample contents are collected by use of millipore filters such as described above. The millipore filter containing the pollutant sample is placed into a test tube or other container and ashed for 2½ hours in a low temperature radio-frequency asher as set forth above.

The ashed sample is then dispersed in an aqueous solution of Aerosol OT at moderate ultrasonic power (60 watts) for about 5 minutes. The total mass of particulate material is reduced by mild centrifugation (10 to 15 g's) for about 30 seconds to eliminate the largest particles. The supernatant suspension is then filtered to collect the asbestos and other fine particles, and washed with deionized water to remove soluble material. The filter and collected asbestos and particulate matter are ashed a second time in a low temperature RF reactor for about 3 hours. Subsequent to ashing the second time, the steps as set forth above for the calibration sample are followed. That is those steps subsequent to ashing the millipore filter starting with adding 30 drops of a 0.001% solution of parlodion in distilled amyl acetate to the ashed residue and sonication thereof. The output signal obtained by the x-ray system is compared with the calibration curve to determine the presence and quantity of asbestos in the obtained sample.

Preparation of the specimen which includes the asbestos particulate matter for use in the x-ray system is carried out by use of the special multielectrode grid, as shown in FIG. 5, wherein the electrodes are interdigitated chromium lines 50$\mu$m wide by 1200 A thickness separated by about 1 mm .

The microelectro assembly is formed in accordance with procedures which are well known in microelectronics such as the following:

1. A "master" is prepared ten times as large as the desired product and photoreduced on a quartz flat.
2. Quartz discs with a 1200-A layer of evaporated chromium are obtained either commercially or from a vacuum evaporation facility. Quartz is desirable because it cleans better than glass and vacuum deposition is more suitable than sputtering due to its more gentle treatment.

3. The discs chromium plated side of the discs are sprayed with photoresist and baked at 300°F for about 15 minutes.
4. The original is placed in contact with the photoresist and exposed to ultraviolet light for about 10 minutes.
5. The exposed disk is "developed" to remove the unexposed photoresist.
6. The exposed chromium is etched away.
7. The photoresist is dissolved and the grid is washed, dried, and inspected for continuity.

The above described method of distinguishing chrysotile asbestos by use of broad beam optics in combination with sample rotation in a plane normal to the x-ray beam by detection with two detectors 90° apart off the axis or by using one detector and rotating the detector is the only known method of distinguishing chrysotile asbestos from other forms of asbestos, by x-ray diffraction technique.

In operation, asbestos fibers are aligned on a substrate by the above method and the substrate is orientated in the x-ray collimator system for maximum diffracted intensity when the fibers are parallel to the axis of the x-ray spectrometer. The x-rays are directed through the collimator onto the asbestos fiber-substrate. The x-rays are diffracted with scattered background onto the detector 15. Simultaneously, the scattered background is recorded by the detector 16. The difference in the two measurements is a measure of the asbestos in the sample.

The system has been shown with two detectors placed 90° apart where one detector detects diffracted x-rays along with background while the other detector detects background. The measurements could be carried out by use of a single detector by first positioning a detector in the position of detector 15 to detect diffracted x-rays and background, then rotating the detector to the position of detector 16. Also, the detector could be left in the position of detector 15 and the sample may be rotated 90° normal with the beam so that the fibers are perpendicular to the spectrometer axis so that the signal and background maybe measured sequentially.

It has been determined that ordinary x-ray diffractometer optics cannot be used or modified to distinguish the chrysotile form even for aligned fibers because of the peculiar "rolled" nature of the asbestos fibers.

In carrying out the method, the asbestos fibers are specifically oriented in substantially parallel alignment on a thin substrate with fibers spread over an area of about one centimeter. Therefore the x-ray beam should have a broad cross section.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method of preparing a sample containing asbestos for the purpose of determining the amount of asbestos in said sample; which comprises, collecting pollutant samples which may contain asbestos on a millipore filter, placing said millipore collected into a test tube and ashing the same for about 2½ hours, dispersing said ashed sample in an aquous solution of dioctyl sodium sulfosuccinate, reducing the total mass of particulate material in said solution by mild centrifugation for about 30 seconds to eliminate the largest particles in said solution, filtering said solution to collect any asbestos and other fine particles and washing with deionized water to remove soluble materials, placing said filter and any asbestos and particulate matter collected thereon into a container and ashing same, subsequent to ashing, dropping 30 drops of a solution containing distilled amyl acetate and 0.001%–002% of cellulose nitrate into the ash residue, sonicating said ash solution to insure a homogeneous distribution of asbestos, placing one drop of said ash solution onto an electrode grid of parallel spaced electrodes having a spacing of about 0.8 mm, applying a voltage to said electrode grid to align said asbestos particles perpendicular to the electrodes of said electrode grid and permitting said solution to dry, spraying a solution of 2.5% cellulose nitrate in amyl acetate onto said dried particles on said electrode grid, permitting said latter solution to dry to form a thin plastic film with said particles embedded therein, stripping said particle embedded plastic film from said electrodes and, placing said particle embedded plastic film onto a ring type holder and permitting same to dry.

2. A method as claimed in claim 1, wherein;

the voltage applied across said electrode grid is about 240 volts.

3. A method as claimed in claim 2, wherein;

said membrane filter has a 0.45 – 0.80$\mu$m pore size to collect a pollutant sample.

* * * * *